United States Patent [19] [11] 4,255,331
MacDonald [45] Mar. 10, 1981

[54] 3-ACETOXY-9β-11β-EPOXY-DIENES AND THE PREPARATION OF THE CORRESPONDING 6α-HALOGEN-4-ENE-3-ONES

[75] Inventor: Peter MacDonald, Arese, Italy

[73] Assignee: Prochem Establishment, Balzers, Liechtenstein

[21] Appl. No.: 26,677

[22] Filed: Apr. 3, 1979

[30] Foreign Application Priority Data

Apr. 5, 1978 [NL] Netherlands .......................... 7803655
Apr. 5, 1978 [NL] Netherlands .......................... 7803656
Mar. 23, 1979 [NL] Netherlands .......................... 7902333

[51] Int. Cl.$^3$ ............................................ C07J 71/00
[52] U.S. Cl. .................. 260/239.55 R; 260/239.55 D
[58] Field of Search ............................... 260/239.55 R

[56] References Cited

U.S. PATENT DOCUMENTS 4,188,322  2/1980  Castelli et al. .................. 260/239.55

FOREIGN PATENT DOCUMENTS 958515  5/1964  United Kingdom ................ 260/397.45

Primary Examiner—Elbert L. Roberts
Attorney, Agent, or Firm—Browdy and Neimark

[57] ABSTRACT

The invention relates to 3-acetoxy-9β,11β,-epoxy-pregna-1,3,5-trienes and the corresponding 3,5-dienes having the general formula 1, in which on the 1,2-position a double bond may be present and in which $R_3$ is a hydrogen or halogen atom or a hyroxy-, acyloxy-, aroyloxy or sulphonyloxygroup; $R_1$ and/or $R_2$ are a hydrogen atom or a hydroxy-, aroyloxy-, acyloxy- or alkyl-group containing 1-6 carbon atoms, or in which $R_1$ and $R_2$ form together a 16,17-isopropylidene-dioxy group, a process for the preparation of this compounds by reacting the corresponding $\Delta^{1,4}$-3-keto-pregnadienes or $\Delta^4$-3-keto-pregnenes with isopropenylacetate and a process for their direct conversion into the corresponding 6α-halogen-substituted-pregna-1,4-diene-3-ones and pregn-4-ene-3-ones with the general formula 2 by reacting them with a positive-halogen producing agent.

14 Claims, No Drawings

3-ACETOXY-9β-11β-EPOXY-DIENES AND THE PREPARATION OF THE CORRESPONDING 6α-HALOGEN-4-ENE-3-ONES

The invention relates to 3-acetoxy-9β,11β-epoxypregna-1,3,5-trienes, the corresponding 3,5-dienes, a process for their preparation and a process for their conversion into 6α-halogen substituted pregna-1,4-diene-3-ones and pregna-4-ene-3-ones.

According to one aspect of the invention 3-acetoxy-9β,11β-epoxypregna-1,3,5-trienes and the corresponding 3,5-dienes having the general formula 1, are described in which on the 1,2-position a double bond may be present and in which $R_3$ is a hydrogen or halogen atom or a hydroxyacyloxy-aroyloxy or sulphonyloxygroup; $R_1$ (in an α- or β-configuration) and/or $R_2$ are a hydrogen atom or a hydroxy-, aroyloxy-, acyloxy- or alkylgroup containing 1–6 carbon atoms, or in which $R_1$ and $R_2$ form together a 16α,17-isopropylidene-dioxy group.

According to another aspect of the invention, a process is described for the direct conversion of these compounds into the corresponding 6α-halogen-substituted pregna-1,4-diene-3-ones and pregna-4-ene-3-ones with the general formula 2, in which X is a halogen atom and $R_1$, $R_2$ and $R_3$ have the meanings as given above.

According to the invention, the new compounds having the general formula 1 are prepared by reacting the corresponding $\Delta^{1,4}$-3-keto or $\Delta^4$-3-keto steroids having the general formula 3 with isopropenylacetate in the presence of a —preferably strong—acid catalyst. The reaction can be carried out in the presence of an inert solvent, but is generally performed without the use thereof. A preferred catalyst is a sulfonic acid, e.g. p-toluene sulfonic acid or a sulfonic acid resin such as Amberlite I R 120. The reaction can be carried out at a temperature ranging between room temperature and the reflux temperature of the mixture. A suitable reaction temperature is 80° C.

The compounds with the general formula 3 can be prepared in a known manner, e.g. as described in "Steroid Reactions" by C. Djerassi, 1963.

Examples of preferred compounds to be prepared according to the invention are the following:

3,17,21-triacetoxy-9β,11β-epoxy-pregna-1,3,5-triene-20-one;

3,17,21-triacetoxy-9β,11β-epoxy-16β-methyl-pregna-1,3,5-triene-20-one;

3,17,21-triacetoxy-9β,11β-epoxy-16α-methyl-pregna-1,3,5-triene-20-one 3,21-diacetoxy-9β,11β-epoxy,16α,17-isopropylidenedioxy-pregna-1,3,5-triene-20-one;

3,17-21-triacetoxy-9β,11β-epoxy-pregna-3,5-diene-20-one;

3,17,21-triacetoxy-9β,11β-epoxy-16β-methyl-pregna-3,5-diene-20-one;

3,17,21-triacetoxy-9β,11β-epoxy-16α-methyl-pregna-3,5-diene-20-one;

3,21-diacetoxy-9β,11β-epoxy-16α,17-isopropylidenedioxy-pregna-3,5-diene-20 one;

3,21-diacetoxy-9β,11β-epoxy-16α-methyl-pregna-3,5-diene-20-one;

3,21-diacetoxy-9β,11β-epoxy-16α-methyl-pregna-1,3,5-triene-20-one;

3-acetoxy-21-valeroyloxy-9β,11β-epoxy-16α-methyl-pregna-1,3,5-triene 20-one;

3-acetoxy-21-hexanoyloxy-9β,11β-epoxy-16α-methyl-pregna-1,3,5-triene-20-one;

3-acetoxy-21-pivaloyloxy-9β-11β-epoxy-16α-methyl-pregna-1,3,5-triene-20-one;

3,21-diacetoxy-17-hydroxy-9β,11β-epoxy-pregna-1,3,5-triene-20-one;

3-acetoxy-21-pivaloyloxy-17-hydroxy-9β,11β-epoxy-16α-methyl-pregna-1,3,5-triene-20-one;

3,21-diacetoxy-17-butyryloxy-9β,11β-epoxy-pregna-1,3,5-triene-20-one;

3,21-diacetoxy-17-propionyloxy-9β,11β-epoxy-pregna-1,3,5-triene-20-one;

3-acetoxy-17-propionyloxy-9β,11β-epoxy-pregna-1,3,5-triene-20-one.

3-acetoxy-17-propionyloxy-21-chloro-16β-methyl-9β,11β-epoxy-pregna-1,3,5-triene-20-one.

β-acetoxy-17-butyoyloxy-9β,11β-epoxy-pregna-1,3,5-triene-20-one 3-acetoxy-17-benzoyloxy-9β,11β-epoxy-pregna-1,3,5-triene-20-one 3-acetoxy-17,21-dipropionyloxy-9β,11β-epoxy-pregna-1,3,5-triene-20-one 3-acetoxy-17-propionyloxy-21-iso-butyoyloxy-9β,11β-epoxypregna-1,3,5-triene-20-one.

3,21-diacetoxy-9β,11β-epoxy-pregna-1,3,5-triene-20-one 3,21-diacetoxy-9β,11β-epoxy-16β-methyl-pregna-1,3,5-triene-20-one It is noted, that the reaction conditions for forming the enol acetates will normally cause any free hydroxyl group to be acetylated. However, it has been found, that by the use of mild conditions (lower temperatures, less catalyst) a 17-hydroxyl group may remain unaffected.

The course of the reaction according to the invention is surprising, since it could be expected that the strongly acidic conditions employed would destroy the acid sensitive epoxy-ring. Further, cross-conjugated dienones such as $\Delta^{1,4}$-3-ketones were previously known to undergo the dienone-phenol rearrangement under acidic acylating conditions (Merck Index, 9th Edition, page ONR-24 and R. Gardi and A. Ercoli in "Organic Reactions in Steroid Chemistry", Editors Fried and Edwards, Volume 1, page 394). Thus, for example, Bailey et al. (J. Chem. Soc. 1961, 4535) describe the aromatization of prednisone acetate, prednisolone acetate and related compounds under acidic acetylating conditions. In this work the acetylating agent used was acetic anhydride in the presence of -toluene sulphonic acid or perchloric acid.

Further, from U.S. Pat. No. 3,047,596 it is also known, that attempts to prepare enol esters of a $\Delta^{1,4}$-3-keto steroid are ordinarily unsuccesful due to the tendency of the $\Delta^{1,4}$-3-pregnadiene-3-ones- to undergo under acidic conditions dienone-phenol rearrangements unless stabilized by a 9α-halogen atom. Therefore, use of the same reaction conditions as described in U.S. Pat. No. 3,047,596 for the enol-acetylation of $\Delta^{1,4}$-3-keto-9β,11β-steroids, without a 9α-halogen atom, would be expected to lead to a complete aromatization.

Barton et al. (Chemical Communications, 1969, 1497 and Nouveau Journal de Chimie 1 (4), 315 (1977)) have described the preparation of enol esters (but not enol acetates) of certain $\Delta^{1,4}$-3-keto steroids, which do not contain a 9β,11β-epoxy group, under strongly basic conditions. Considering the bases used (metal alkyls) this method would not be applicable to 9β,11β-epoxy steroids, nor to corticosteroids in general unless the sensitive side chain is protected as the 17,20; 20,21-bis-methylenedioxy(BMD) derivative. The reaction conditions described in the present invention have previously been used for the enol-acetylation of saturated 3,17 and 20-ketones, as well as Δ$^4$-3-ketones not containing a 9β,11β-epoxy group (Fieser and Fieser, "Reagents for Organic Synthesis", John Wiley (1968), but have not previously been applied to Δ$^{1,4}$-3-keto steroids.

The compounds prepared according to the invention are particularly suitable for the preparation of the corresponding 6α-halogen-substituted pregna-1,4-diene-3-ones and pregna-4-ene-3-ones. Hitherto 6-α-halogen substituted Δ$^{1,4}$-3-keto-steroids have usually been obtained from Δ$^5$-3-hydroxy compounds by lengthy and expensive procedures which normally require microbiological introduction of the Δ$^1$-group. Previously no practical method has been available for converting readily available Δ$^{1,4}$-3-ketones into their valuable 6α-halogen-substituted derivatives. Thus Barton et al. describe in Nouveau Journal de Chemie, Vol. 1, no. 4, 315–321 (1977), that halogenation of a Δ$^{1,3,5}$-3-enolbenzoate leads practically only to the formation of the 6β-derivative, which cannot be converted to its 6α-epimer. In the Δ$^4$-pregnenes a method is known in which the corresponding enolacetates are halogenated, but this invariably leads predominantly to the 6β-halogen-derivatives, which then must be epimerized to the 6α-halogen derivatives in a subsequent step (see e.g. U.S. Pat. No. 2,961,441; Chem. and Ind. 1959, 137 and "Organic Reactions in Steroid Chemistry", edited by Fried and Edwards Vol. I, 1972, p. 475).

Surprisingly, it has been found that introduction of a 6-halogen-substituent into a 3-acetoxy-Δ$^{1,3,5}$-triene or 3-acetoxy-Δ$^{3,5}$-diene which contains a 9β,11β-epoxy group leads exclusively to the corresponding 6α-substituted Δ$^{1,4}$-diene-3-one or Δ$^4$-ene-3-one. According to the invention, these compounds are prepared by treating the compounds with formula 1, wherein R1,R2 and R3 have the meanings as given above and in which a double bond may be present in the 1,2-position, with a positive-halogen producing agent.

It is remarked, that in the U.S. Pat. No. 3,047,596 (corresponding with dutch patent 129 640) the chlorination and bromination of Δ$^{1,3,5}$-enolesters without a 9β,11β-epoxygroup is described. As is made clear by the article of Barton et al. in Nouveau Journal de Chemie, vol. I no. 4, 315–321 and which has been confirmed in the following comparative example this invariably leads mainly to the formation of the undesirable 6β-halogen-derivative.

Suitable positive halogen producing reagents for the halogenation of this invention are: N-bromosuccinimide, N-bromoacetamide, 1,3-dibromo-5,5-dimethylhydantoine, bromine, N-chlorosuccinimide, N-chloroacetamide, 1,3-dichloro-5,5-dimethylhydantoine, chlorine, perchlorylfluoride, fluorine, fluoroxytrifluoromethane.

As reaction conditions may be selected such as are conventional for the introduction of halogen substituents. The reaction can for instance be carried out in an aqueous solution, containing a water-miscible organic solvent, in which the steroid is soluble. Preferably a base is present. Suitable organic solvents are for instance acetone, dioxane, ethanol, tetrahydrofurane etc. Suitable bases are pyridine, triethylamine or potassium acetate. The reaction can be carried out at a temperature between −80° and +30° C., depending upon the halogenating agent used.

For the preparation of 6α-chloro-compounds the preferred chlorinating agent is chlorine. The reaction is conducted by leading chlorine gas through a solution of the steroid in 65% aqueous dioxane, eventually containing a trace of pyridine at a temperature of preferably about −10° to 0° C.

For the preparation of 6α-fluoro compounds the preferred fluorinating agent is perchlorylfluoride. This compound is added to the reaction mixture as a gas and preferably lead through the solution of the steroid in ethanol containing potassium acetate at a temperature of −10° to +20° C. It has been observed that under certain conditions the reaction of perchloryl fluoride with the Δ$^{3,5}$- and Δ$^{1,3,5}$-enol acetates may produce, in addition to the desired 6α-fluoro-pregna-4-ene-3-ones and 6α-fluoro-pregna-1,4-diene-3-ones, a variable amount of the corresponding 6α-chloro analogues, which are usually separable from the desired product only with extreme difficulty. Under the preferred reaction conditions, however, no significant amounts of the 6α-chloro by-products are formed.

Preferred compounds which can be prepared in accordance with this aspect of the invention are: 9β,11β-epoxy-6α-fluoro-17α,21-diacetoxy-pregna-1,4-dienes-3,20-dione;

9β,11β-epoxy-6α-fluoro-17α,21-diacetoxy-4-pregnen-3,20-dione;

9β,11β-epoxy-6α-fluoro-21-acetoxy-16α,17-isopropylidenedioxy-pregna-1,4-dien-3,20-dione;

9β,11β-epoxy-6α-fluoro-21-acetoxy-16α,17-isopropylidene-dioxy-4-pregnen-3,20-dione;

9β,11β-epoxy-6α-fluoro-17,21-diacetoxy-16α-methyl-pregna-1,4-diene-3,20-dione;

9β,11β-epoxy-16α-fluoro-17,21-diacetoxy-16α-methyl-4-pregnen-3,20-dione;

9β,11β-epoxy-6α-fluoro-17,21-diacetoxy-16β-methyl-4-pregnen-3,20-dione;

9β,11β-epoxy-6α-fluoro-17,21-diacetoxy-16β-methyl-pregna-1,4-diene-3,20-dione;

9β,11β-epoxy-6α-chloro-17,21-diacetoxy-pregna-1,4-diene-3,20-dione;

9β,11β-epoxy-6α-chloro-17,21-diacetoxy-16α-methyl-pregna-1,4-diene-3,20-dione;

9β,11β-epoxy-6α-chloro-17,21-diacetoxy-16β-methyl-pregna-1,4-diene-3,20-dione;

9β,11β-epoxy-6α-chloro-21-acetoxy-16α,17-isopropylidene-dioxy-pregna-1,4-diene-3,20-dione;

9β,11β-epoxy-6α-fluoro-21-acetoxy-16α-methyl-pregna-1,4-diene-3,20-dione;

9β,11β-epoxy-6α-fluoro-21-hexanoyloxy-16α-methyl-pregna-1,4-diene-3,20 dione;

9β,11β-epoxy-6α-fluoro-21-pivaloyloxy-16α-methyl-pregna-1,4-diene-3,20-dione;

9β,11β-epoxy-6α-fluoro-21-valeroyloxy-16α-methyl-pregna-1,4-diene-3,20-dione;

9β,11β-epoxy-6α-fluoro-21-acetoxy-17-hydroxy-pregna-1,4-diene-3,20-dione;

9β,11β-epoxy-6α-fluoro-21-pivaloyloxy-17-hydroxy-16α-methyl-pregna-1,4-diene-3,20-dione;

9β,11β-epoxy-6α-fluoro-21-acetoxy-17-butyryloxy-pregna-1,4-diene-3,20-dione;

9β,11β-epoxy-6α-fluoro-21-acetoxy-17-propionyloxy-pregna-1,4-diene-3,20-dione;

9β,11β-epoxy-6α-fluoro-17-propionyloxy-pregna-1,4-diene-3,20-dione;

9β,11β-epoxy-6α-fluoro-21-chloro-17-propionyloxy-16β-methylpregna-1,4-diene-3,20-dione.

9β,11β-epoxy-6α-fluoro-21-acetoxy-pregna-1,4-diene-3,20-dione;

9β,11β-epoxy-6α-fluoro-21-acetoxy-16β-methyl-pregna-1,4-diene-3,20-dione;

9β,11β-epoxy-6α-fluoro-17-benzoyloxy-pregna-1,4-diene-3,20-dione;

9β,11β-epoxy-6α-fluoro-17,21-dipropionyloxy-pregna-1,4-dione-3,20-dione;

9β,11β-epoxy-6α-fluoro-17-butyryloxy-pregna-1,4-diene-3,20-dione;

9β,11β-epoxy-6α-fluoro-21-iso-butyryloxy-17-propionyloxy-pregna-1,4-diene-3,20-dione.

The compounds having the general formula 2 can be easily converted by known methods into valuable corticoids, for example by converting the epoxy group into a 9α-halogen-11β-hydroxy compound having the general formula 4, wherein Y is a halogen atom and X, $R_1$, $R_2$ and $R_3$ have the meanings as given above, and using for example the reaction conditions as described by Fried and Sabo in the Journal of the American Chemical Society, 75, 2273 (1953), or in "Steroids" by L. F. Fieser and M. Fieser, page 680-686. Thus, for example, clocortolone-21-pivalate is obtained by treating 9β,11β-epoxy-6α-fluoro-21-pivaloyloxy-16α-methyl-pregna-1,4-diene-3,20-dione with hydrogenchloride; fluocinonide is obtained by treating 9β,11β-epoxy-6α-fluoro-21-acetoxy-16α,17-isopropylidenedioxy-pregna-1,4-diene-3,20-dione with hydrogenfluoride. Conventional alkaline hydrolysis of fluocinonide then leads to fluocinolone-acetonide. Further, fluomethasone pivalate can be obtained by treating 9β,11β-epoxy-6α-fluoro-21-pivaloyloxy-17-hydroxy-16α-methyl-pregna-1,4-diene-3,20-dione with hydrogen fluoride. Other well known compounds such as flumethasone-17,21-diacetate, diflorasone-17,21-diacetate, 6α,9α-difluoro-prednisolone-17-butyrate-21-acetate-6α,9α-difluoroprednisolone-17,21-dipropionate, difluorocortolone-21 valerate, flumethasone, 6α,9α-difluoroprednisolone 17-propionate-21 acetate, 6α,9α-difluoroprednisolone 17 propionate 21-iso-butyrate, 6α,9α-difluoro-21-desoxyprednisolone 17-propionate, 6α,9α-difluoro-21-desoxyprednisolone-17-butyrate, 6α,9α-difluoro-21-desoxyprednisolone 17-benzoate fluocinolone acetonide 21-propionate and other 21-esters may be obtained by treatment of the products obtained in accordance with the invention with hydrogen fluoride, optionally followed by conventional hydrolysis with alkali and/or esterification.

Other important corticoids unsubstituted in position 9 having the general formula 4, wherein Y is a hydrogen atom and X, $R_1$, $R_2$ and $R_3$ have the meanings as given above, can be obtained by treatment of the products obtained in accordance with the invention with a hydrogen halide preferably hydrogen bromide, followed by subsequent dehalogenation, for example, as described in U.S. Pat. No. 3,894,063. Thus, for example, treatment of 9β,11β-epoxy-6α-fluoro-21-acetoxy-16α,17-isopropylidene dioxy-pregna-1,4-diene-3,20-dione with hydrogen bromide followed by treatment with tributylthinhydride leads to flunisolide acetate. Similar treatment of 9β,11β-epoxy-6α-fluoro-21-acetoxy-16α,17-isopropylidenedioxy-pregn-4-ene-3,20-dione leads to flurandrenolide acetate, from which flurandrenolide may be obtained by convertional alkaline hydrolysis.

Other well known compounds, such as paramethasone acetate, flunisolide, fluocortolone-21-hexanoate, fluprednisolone or 6α-chloroprednisone-21-acetate may be obtained by similar hydro-halogenation, followed by selective dehalogenation, optionally followed by conventional hydrolysis with alkali and/or esterification and/or oxidation, for example, with Jones reagent of the 11β-hydroxygroup.

The invention is illustrated in and by the following examples.

EXAMPLE I

To a stirred suspension of 17.1 g of 9β,11β-epoxy-21-acetoxy-16α,17-isopropylidenedioxy-pregna-1,4-diene-3,20-dione, prepared as described in Dutch patent application 7 117 203, in 85,5 ml of isopropenyl acetate was added 2.56 g of p-toluene sulfonic acid and the mixture was stirred at 80°-85° C. for 3.5 hr with exclusion of moisture. The resulting solution was cooled, neutralized with pyridine (5 ml) and evaporated to a form (24.8 g), which crystallized from aqueous dioxane containing a trace of pyridine. The suspension was kept at 5° C. overnight and the colourless granular crystals were collected, rinsed with methanol-pyridine (19:1) and then with ether and dried under vacuum. Yield: 16.6 g 9β,11β-epoxy-3,21-diacetoxy-16α,17-isopropylidenedioxy-pregna-1,3,5-triene-20-one. A sample (5g) was twice crystallized from methanol (0.5% pyridine) to give the analytical sample which had the following characteristics:

melting point: 177° C.
$\lambda_{max}^{MeOH}$ 316 nm ($\epsilon$=3300)
$[\alpha]_D$ —197° (c=1, dioxane)
$\nu_{max}$: 1750, 1735, 1650, 1620, 1580, 1240-1200 cm$^{-1}$.

EXAMPLE II 10 g of sulfonic acid resin (Amberlite I R120, marketed by Rohm and Haas Co.) was dehydrated by azeotropic destillation with benzene. The dry resin was suspended in 50 ml isopropenylacetate and 10 g 9β,11β-epoxy-21-acetoxy-17-hydroxy-pregna-1,4-diene-3,20-dione were added. The mixture was heated under reflux for 5 hours, cooled and filtered an the filtrate was evaporated to dryness. The residue which crystallized from methanol (0,5% pyridine) gave in high yield (9,5 grams) 3,21-diacetoxy-17-hydroxy-9β,11β-epoxy-pregna-1,3,5-triene-20-one. Melting point: 194° C., $\lambda_{max}$310 nm ($\epsilon$5500).$[\alpha]_D$ in chloroform —199° C. (c=1% chloroform), $\nu_{max}$(cm$^{-1}$) (K Br) 3450; 1765; 1740; 1725; 1655; 1625; 1590.

The same product was obtained, when the catalyst was p-toluenesulphonic acid (0.5 g) and the reaction was performed at 50° C. for 10 minutes.

EXAMPLE III

To a solution of 2 g p-toluene sulfonic acid in 100 ml isopropenylacetate was added 20 g of 9β,11β-epoxy-21-acetoxy-17-hydroxypregna-1,4-diene-3,20-dione and the mixture was kept at 80°-85° C. for 2.5 hr with exclusion of moisture. The resulting solution was cooled, neutralized with pyridine (3 ml) and evaporated under high vacuum to give crude 9β,11β-epoxy-3,17,21-triacetoxy-pregna-1,3,5-trien-20-one as a hard gum (25 g) which could not be induced to crystallize ($\lambda_{max}$301 nm $\epsilon$=5400).

EXAMPLE IV

Using the procedure as described in Example III but starting from 9β,11β-epoxy-16α-methyl-21-acetoxy-17-hydroxypregna-1,4-diene-3,20-dione there was obtained 26 g 9β,11β-epoxy-16α-methyl-3,17,21-triacetoxy-pregna-1,3,5-trien-20-one as an amorphous solid having $\lambda_{max}$302 nm ($\epsilon$=5500).

EXAMPLE V

Using the procedure as described in Example IV but starting from 9$\beta$,11$\beta$-epoxy-16$\beta$-methyl-21-acetoxy-17-hydroxypregna-1,4-diene-3,20-dione there was obtained 25,5 g 9$\beta$,11$\beta$-epoxy-16$\beta$-methyl-3,17,21-triacetoxy-prgena-1,3,5-triene-20-one as an amorphous solid having $\lambda_{max}$301 nm ($\epsilon$=5200).

EXAMPLE VI

Using the procedure as described in Example I, but starting from 10 g 9$\beta$,11$\beta$-epoxy-21-pivaloyloxy-17-hydroxy-16$\alpha$-methyl-pregna-1,4-diene-3,20-dione and using a temperature of 50° C. and a reaction time of 30 minutes there was obtained 8,5 g of 3-acetoxy-9$\beta$,11$\beta$-epoxy-21-pivaloyloxy-17-hydroxy-16$\alpha$-methyl-pregna-1,3,5-triene-21-one. Melting point: 108°-120° C.; $\lambda_{max}$: 305 nm ($\epsilon$4700).

EXAMPLE VII

Using the procedure as described in Example I, but starting from 4 g 9$\beta$,11$\beta$-epoxy-21-acetoxy-16$\alpha$-methyl-pregna-1,4-diene-3,20-dione there was obtained as a crystalline residue 3,8 g of 3,21-diacetoxy-9$\beta$,11$\beta$-epoxy-16$\alpha$-methyl-pregna-1,3,5-triene-20-one.

$\lambda_{max}$: 306 nm ($\epsilon$=5000)
$\nu_{max}$ (cm$^{-1}$) (K Br) 1750; 1720; 1655; 1615; 1585.

EXAMPLE VIII (comparative Example)

A mixture of 26,0 g triamcinolone acetonide 11,21-diacetate, prepared as described in British Pat. No. 1 375 770, 10,40 g p-toluene sulfonic acid and 130 ml isopropenyl acetate was heated for 4 hours under reflux conditions and with exclusion of moisture. After cooling to room temperature the mixture crystallized and after 16 hours the crystals were collected, washed with a cold methanol solution containing 0.5% pyridine, and then dried under vacuum at 40° C. Yield: 21 g 9$\alpha$-fluoro-3,11$\beta$,21-triacetoxy-16$\alpha$,17-isopropylidenedioxy pregna-1,3,5-triene-20-one. Melting point: 196° C.; $\lambda_{max}$305 nm ($\epsilon$6700)

$[\alpha]_D$-136,5 (c=1, dioxan)
$\nu_{max}$: 1760, 1750, 1725, 1630, 1235-1205 cm$^{-1}$ A solution of 15 g of this compound, in 200 ml dioxane, 90 ml water and 10 ml pyridine was cooled to $-10°$ C. and treated with 4 g perchlorylfluoride during 4 hours. Then the temperature of the solution was adjusted to 0° C., which temperature was maintained during another 4 hours. The reaction solution was poured into an ice-cold solution of 15 g sodium bicarbonate in 60 ml water and after stirring during 2 hours at a temperature of 0°-5° C. the precipitate was collected and washed with water to neutral. After drying in vacuum 14 g of a mixture containing 10% fluocinolone acetonide 11,21-diacetate (see British patent specification No. 1 375 770) and 90% of the 6$\beta$-epimer was obtained.

EXAMPLE IX 15 g 9$\beta$,11$\beta$-epoxy-3,17,21-triacetoxy-pregna-1,3,5-triene-20-one, prepared as described in Example III, were dissolved in 300 ml of absolute ethanol containing 15 g of potassium acetate. The mixture was treated at 0°-5° C. with a slow stream of perchlorylfluoride during 3 hours, whereafter 4 g of gas had been absorbed. The reaction mixture was kept at 5° C. for a further 14 hours and then poured into a large volume of water. The precipitate which formed was collected and washed with water to neutral.

After drying in vacuo, 14 g 9$\beta$,11$\beta$-eopoxy-6$\alpha$-fluoro-1,4-pregnadien-17$\alpha$,21-diacetoxy-3,20-dione were obtained.

After recrystallisation from methanol a sample having the following physical properties was obtained: melting point: 229° C.

TLC: (Merck silicagel F$_{254}$/benzene/ether 1:1 R$_F$ 0,55)

$\lambda_{max}$246 nm ($\epsilon$16500)
$[\alpha]_D$+19° (c=1, dioxane).
$\nu_{max}$: 1745, 1730, 1665, 1630, 1605, 1230 cm$^{-1}$.

EXAMPLE X

Using the procedure as described in Example IX, but starting from 15 g 9$\beta$,11$\beta$ epoxy-3,17,21-triacetoxy-16$\alpha$-methyl-pregna-1,3,5-triene-20-one as prepared in Example IV there was obtained 13,5 g of 9$\beta$,11$\beta$-epoxy-6$\alpha$-fluoro-17,21-diacetoxy-16$\alpha$-methyl-pregna-1,4-diene-3,20-dione.

Melting Point: 175° C.
$\lambda_{max}$: 244 nm ($\epsilon$=16850)
$[\alpha]_D$+6° (c=1, dioxan)
$\nu_{max}$: 1745; 1675; 1640; 1610.

EXAMPLE XI

Using the procedure as described in Example IX, but starting from 15 g 9$\beta$,11$\beta$-epoxy-3,17,21-triacetoxy-16$\beta$-methyl-pregna-1,3,5-triene-20-one prepared as described in Example V, there was obtained 13,6 g of 9$\beta$,11$\beta$-epoxy-6$\alpha$-fluoro-17,21-diacetoxy-16$\beta$-methyl-pregna-1,4-diene-3,20-dione. After recrystallization from ether, the following physical characteristics were found:

Melting point: 229° C. (decomposition)
$\lambda_{max}$: 244 nm ($\epsilon$=16800)
$[\alpha]_D$: +10° (c=1, dioxan)
$\nu_{max}$: 1755, 1730, 1665, 1630, 1610 cm$^{-1}$.

EXAMPLE XII 15 g 9$\beta$,11$\beta$-epoxy-3,21-diacetoxy-16$\alpha$,17-isopropylidenedioxy-pregna-1,3,5-triene-20-one, prepared as described in Example I was treated as described in Example IX and gave 13 g 9$\beta$,11$\beta$-epoxy-6$\alpha$-fluoro-21-acetoxy-16$\alpha$,17-isopropylidene-dioxy-pregna-1,4-diene-3,20-dione.

Melting point: 235° C.
$\lambda_{max}$245 nm ($\epsilon$=15750)
$[\alpha]_D$+60° (c=1, dioxan)
$\nu_{max}$: 1760; 1740; 1680; 1640; 1615; 1240 cm$^{-1}$

EXAMPLE XIII 17,5 g of 9$\beta$,11$\beta$-epoxy-3,17,21-triacetoxy-pregna 3,5-diene-20-one, prepared as described in Example I were dissolved in a mixture of 200 ml dioxane, 90 ml water, 10 ml pyridine, with the temperature being maintained at $-10°$ C. Next a total quantity of approximately 4 g perchlorylfluoride was introduced at this temperature over a period of 4 hours. The further procedure was as described in Example IX; 16 g 9$\beta$,11$\beta$-epoxy-6$\alpha$-fluoro-17$\alpha$,21-diacetoxy-4-pregnen-3,20-dione were obtained.

Physical data:
melting point: 225° C. (decomposition).
$\lambda_{max}$=234 nm ($\epsilon$=14000).
$\nu_{max}$: 1745, 1730, 1680, 1630, 1240 cm$^{-1}$.

EXAMPLE XIV

Under using the method as described in Example I and starting from 14 g 9β,11β-epoxy-21-acetoxy-16α,17-isopropylidenedioxy-pregn-4-ene-3,20-dione, there was obtained 15 g of 9β,11β-epoxy, 3,21-diacetoxy-16α,17-isopropylidenedioxy-pregna-3,5-diene-20-one, which on treatment as described in Example IX with perchlorylfluoride gave 12 g 9β,11β-epoxy-6α-fluoro-21-acetoxy-16α,17-isopropylidenedioxy-4-pregnen-3,20-dione. Mp.: 223° C.; λ$_{max}$234 nm (ε=13600)

ν$_{max}$: 1750, 1730, 1675, 1620, 1230 cm$^{-1}$.

EXAMPLE XV 3 g 3,21-diacetoxy-9β,11β-epoxy-16α-methyl-pregna-1,4-diene-3,20-dione, obtained as described in Example V, were treated with perchlorylfluroide according to the conditions of Example IX, to give 2 g of 6α-fluoro-9β,11β-epoxy-21-acetoxy-16α-methyl-pregna-1,4-diene-3,20-dione.

Melting point: 154°–162° C.;
λ$_{max}$247 nm (ε=15000)
ν$_{max}$ (cm$^{-1}$) (K Br): 1750; 1725; 1665; 1630; 1610.

EXAMPLE XVI

To a solution at 0° of 3,21-diacetoxy-9β,11β-epoxy-16α,17-isopropylidenedioxy-pregna-1,3,5-triene-20-one (20 g prepared as described in Example I) in 65% aqueous dioxan (400 ml) containing pyridine (20 ml) was added slowly chlorine gas until thin-layer-chromatography demonstrated the absence of starting material. The solution was then poured slowly into a large volume of water and the resulting precipitate of 9β,11β-epoxy-6α-chloro-21-acetoxy-16α,17-isopropylidenedioxy-pregna-1,4-diene-3,20-dione was collected, washed with water and dried under vacuum. Yield 19,5 g. A sample which was crystallized from ether had the following characteristics:

melting point: 211° C.
λ$_{max}$245 nm (ε16.800)
[α]$_D$+57.5° (c=1, dioxan)
ν$_{max}$: 1750, 1720, 1660, 1625, 1600, 1230 cm$^{-1}$

EXAMPLE XVII 20 g of 3,17,21-triacetoxy-9β,11β-epoxy-pregna-1,3,5-triene-20-one, obtained as in Example III were treated with chlorine gas, exactly as described in Example XVI. There was obtained 19.2 g of 9β,11β-epoxy-6α-chloro-17,21-diacetoxy-pregna-1,4-diene-3,20-dione, which crystallized from methanol to give 15 g of colourless crystals.

Melting point: 255° C.
λ$_{max}$246 nm (ε16000)
[α]$_D$0° (c=1, dioxan);
ν$_{max}$: 1760, 1740, 1675, 1640, 1620, 1245 cm$^{-1}$

EXAMPLE XVIII 15 g of 3,17,21-triacetoxy- 9β,11β-epoxy-16α-methylpregna-1,3,5-triene-20 one, obtained as in Example IV, were treated with chlorine gas, as in Example XVI. There were obtained 13,5 g of 9β,11β-epoxy-6α-chloro-17,21-diacetoxy-16α-methyl-pregna-1,4-diene-3,20-dione which crystallized from ether:

melting point 211° C. with decomposition
λ$_{max}$ 246 nm (ε16.100)
[α]$_D$-7.5° (c=1, dioxan)
ν$_{max}$: 1750, 1740, 1675, 1640, 1620, 1240 cm$^{-1}$.

The following example demonstrate how the products of the invention may be converted into 9α-halo-substituted corticoids.

EXAMPLE XIX

To a mixture of anhydrous hydrogen fluoride (20 g) in tetrahydrofuran (40 ml) at −5° was added a solution of 6 g of the 6 α-fluoro-epoxide obtained in Example XI and the resultant solution was kept at −5° to 0° to 0° for 20 hours and then poured out into water and neutralized with potassium arbonate. Extraction with chloroform and crystallization from methanol gave 4,6 g of diflorasone diacetate.

In a similar manner the 6α-fluoro-epoxides obtained in Examples IX, X, XII and XV gave in high yields 6α,9α-difluoroprednisolone 17,21-diacetate, flumethasone diacetate fluocinonide (fluocinolone acetonide acetate), and difluorocortolone 21-acetate respectively.

Similarly, treatment of the 6α-fluoro-epoxide obtained in example XV with hydrochloride acid in chloroform at 0° yielded clocortolone 21-acetate.

The following example demonstrate how the products of the invention may be converted into 9α-unsubstituted corticoids.

EXAMPLE XX

To a solution of 10 g of the 6α-fluoro-epoxide obtained in Example XVI in 100 ml of glacial acetic acid was added hydrogen bromide (1,03 mole) at 20° C. After 30 min. the reaction mixture was poured into water to give in quantitative yield the corresponding bromohydrin,21-acetoxy-11β-hydroxy-16α,17-isopropylidenedioxy-6α-fluoro-9α-bromo-pregna-4-ene-3,20-dione. Reaction of 10 g of this bromohydrin under anhydrous conditions in tetrahydrofuran with a dehalogenating agent, for example, tributyltin hydride, gave 7,5 g of flurandrenolide acetate.

In a similar manner the 6α-fluoro-epoxides obtained in examples IX,X,XII,XII,XV and XVII were converted in high yields into fluprednisolone 17,21-diacetate, paramethasone 17,21 diacetate, flunisolide 21-acetate, 6α-fluoro-hydrocortisone 17,21-diacetate, fluocortolone 21-acetate and 6α-chloroprednisolone diacetate. Oxidation of the latter compound using Jones reagent gave 6α-chloro-prednisone diacetate.

I claim:

1. 3-acetoxy-9β,11β-epoxy-pregna-3,5-dienes having the general formula:

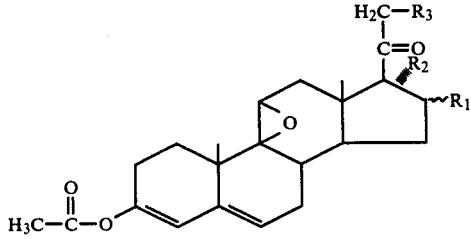

in which R$_3$ is a hydrogen or halogen atom or a hydroxy, acyloxy, aroyloxy- or sulphonyloxy group; and in which R$_1$ which may be α- or β-, and/or R$_2$ are a hydrogen atom or a hydroxy-, aroyloxy-, acyloxy or alkyl group containing 1-6 carbon atoms, or in which R$_1$ and R$_2$ form together a 16,17-isopropylidene-dioxy group.

2. 3,17,21-triacetoxy-9β,11β-epoxy-pregna-3,5-diene-20-one in accordance with claim 1.

3. 3,17,21-triacetoxy-9β,11β-epoxy-16β-methyl-pregna-3,5-diene-20-one in accordance with claim 1.

4. 3,17,21-triacetoxy-9β,11β-epoxy-16α-methyl-pregna-3,5-diene-20-one in accordance with claim 1.

5. 3,21-diacetoxy-9β,11β-epoxy-16α,17-isopropylidenedioxy-pregna-3,5-diene-20-one in accordance with claim 1.

6. 3,21-diacetoxy-9β,11β-epoxy-16α-methyl-pregna-3,5-diene-20-one in accordance with claim 1.

7. A process for preparing compounds in accordance with claim 1, characterized in that the corresponding Δ4-3-keto-pregnenes having the general formula:

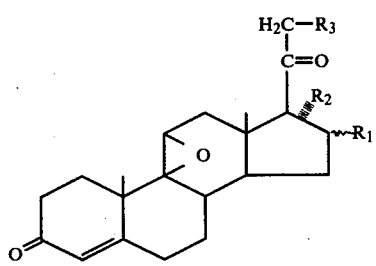

wherein $R_1$, $R_2$ and $R_3$ have the meanings as given above, are reacted with isopropenyl acetate in the presence of an acid catalyst and optionally in the presence of an inert solvent and at a temperature ranging between room temperature and the reflux temperature of the mixture.

8. A process according to claim 7, characterized in using as the catalyst a sulfonic acid resin.

9. A process according to claim 7, characterized in using as the catalyst p-toluene-sulfonic acid.

10. A process according to claim 7, characterized in that no solvent is used.

11. A process according to claim 7, characterized in that the reaction is carried out at a temperature of about 80° C.

12. A process for the preparation of 6α-halo-substituted-pregna-4-ene-3-ones, having the general formula:

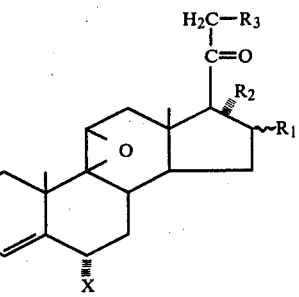

in which X is a α-halogen atom, and $R_3$ is a hydrogen or halogen atom or a hydroxy-, acyloxy-, aroyloxy- or sulphonyloxy group, and in which $R_1$ which may be α- or β-, and/or $R_2$ are a hydrogen atom or a hydroxy-, aroyloxy, acyloxy or alkyl group containing 1–6 carbon atoms, or in which $R_1$ and $R_2$ form together a 16,17-isopropylene-dioxy group, characterized in that a compound having the general formula

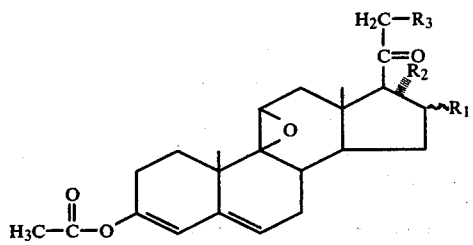

in which $R_1$, $R_2$ and $R_3$ have the meanings as given above, is treated with a positive halogen producing agent.

13. A process according to claim 12, characterized in that for the preparation of 6α-fluoro compounds, perchlorylfluoride is used as halogenating agent and the reaction is carried out in ethanol in the presence of potassium acetate at a temperature between about 0° C. and 20° C.

14. A process according to claim 12, characterized in that for the preparation of 6α-chloro-compounds chlorine gas is used as halogenating agent which is lead through a solution of the steroid in 65% aqueous dioxane, at a temperature between about −10° C. and 0° C.

* * * * *